United States Patent [19]

McFall

[11] Patent Number: 5,446,595

[45] Date of Patent: Aug. 29, 1995

[54] LOOSE STONE DETECTOR

[76] Inventor: Joseph L. McFall, 1900 Pelican Landing Blvd., Apt. 1013, Clearwater, Fla. 34622

[21] Appl. No.: 330,548

[22] Filed: Oct. 28, 1994

[51] Int. Cl.$^6$ .................. G02B 27/02; G01N 21/87
[52] U.S. Cl. .................................. 359/804; 356/30; 84/464 R
[58] Field of Search ............... 359/804, 805, 800, 798, 359/808, 804, 810, 811; 84/464 R; 356/30

[56] References Cited

U.S. PATENT DOCUMENTS

| | | | |
|---|---|---|---|
| 4,158,982 | 6/1979 | Chusid | 84/464 R |
| 5,260,763 | 11/1993 | Yamashita | 356/30 |

Primary Examiner—Loha Ben
Attorney, Agent, or Firm—Stanley M. Miller

[57] ABSTRACT

A device for detecting loose stones in a jewelry setting includes a pedestal against which a ring or other jewelry item is lightly held, and a vibrator for causing vibration of the pedestal and hence of the jewelry item held against it. A large magnifying lens is positioned a few inches above the pedestal so that the owner of the jewelry item may observe the stones when the setting is vibrated. This enables a jeweler's customer to see loose stones themselves without relying upon the opinion of the jeweler. The vibrator is a motor contained within a housing, and the pedestal extends upwardly through an aperture formed in a top wall of the housing. A linkage means interconnects the output shaft of the motor and the pedestal in such a way as to cause vibration of the pedestal. A light mounted above the pedestal illuminates it, and separate switch actuators are provided for the actuation of the motor and the light. The magnifying lens is spaced apart from the pedestal by a spacer wall having a height substantially equal to the focal length of the magnifying lens.

7 Claims, 2 Drawing Sheets

LOOSE STONE DETECTOR

BACKGROUND OF THE INVENTION

1. Field of the invention

This invention relates, generally, to tools used by jewelers. More particularly, it relates to a tool that facilitates visual verification of loose stones in a setting.

2. Description of the prior art

Jewelers typically examine customer's stones through an eyepiece that magnifies the setting for the benefit of the jeweler. The customer, however, cannot see the stone through the eyepiece and must rely on the report of the jeweler as to what was observed through the eyepiece. Some customers may not believe the jeweler's report, and some customers want to view the setting through the eyepiece so that they can see the condition of the stone or stones themselves. Unfortunately, it often requires a trained eye to see defects, so allowing a customer to peer through the eyepiece does not always satisfy the customer that work needs to be done. Even new jewelers require training before they can effectively use a jeweler's eyepiece.

What is needed, then, is an improved means for enabling novice jewelers and members of the public to examine stones under a magnifying glass. The improved means should enable the customer to see loose stones easily. However, in view of the state of the jeweler's art at the time the present invention was made, it was not obvious to those of ordinary skill in said art how such an improved means could be provided.

SUMMARY OF THE INVENTION

The longstanding but heretofore unfulfilled need for an improved means for inspecting stones has now been fulfilled by a device that can be used by novice jewelers and laypersons. The novel device includes a magnifying lens, having a breadth of several inches, positioned several inches above a base member. The base member is provided in the form of a parallelpiped housing that houses a vibrating means. A pedestal connected to the vibrating means extends through an aperture formed in a top wall of the housing so that a jewelry item positioned in abutting relation to said pedestal is vibrated when the pedestal is vibrated. A first switch actuator activates the vibrating means and a second switch actuator activates a lighting means that illuminates the pedestal area to facilitate viewing of the jewelry item as it undergoes vibration.

Although the base member and magnifying lens are preferably disposed in a substantially horizontal plane, they could be mounted in any other plane.

The primary object of this invention is to facilitate observation of an item of jewelry as it undergoes vibration.

Another object is to provide a tool usable by jeweler's customers so that said customers can observe for themselves the condition of their jewelry items.

These and other important objects, advantages, and features of the invention will become apparent as this description proceeds.

The invention accordingly comprises the features of construction, combination of parts, and arrangement of elements set forth hereinafter, and the scope of the invention will be indicated in the claims.

BRIEF DESCRIPTION OF THE DRAWINGS

For a fuller understanding of the nature and objects of the invention, reference should be made to the following detailed description, taken in connection with the accompanying drawings within which.

DETAILED DESCRIPTION OF THE PREFERRED EMBODIMENT

Figure 1:
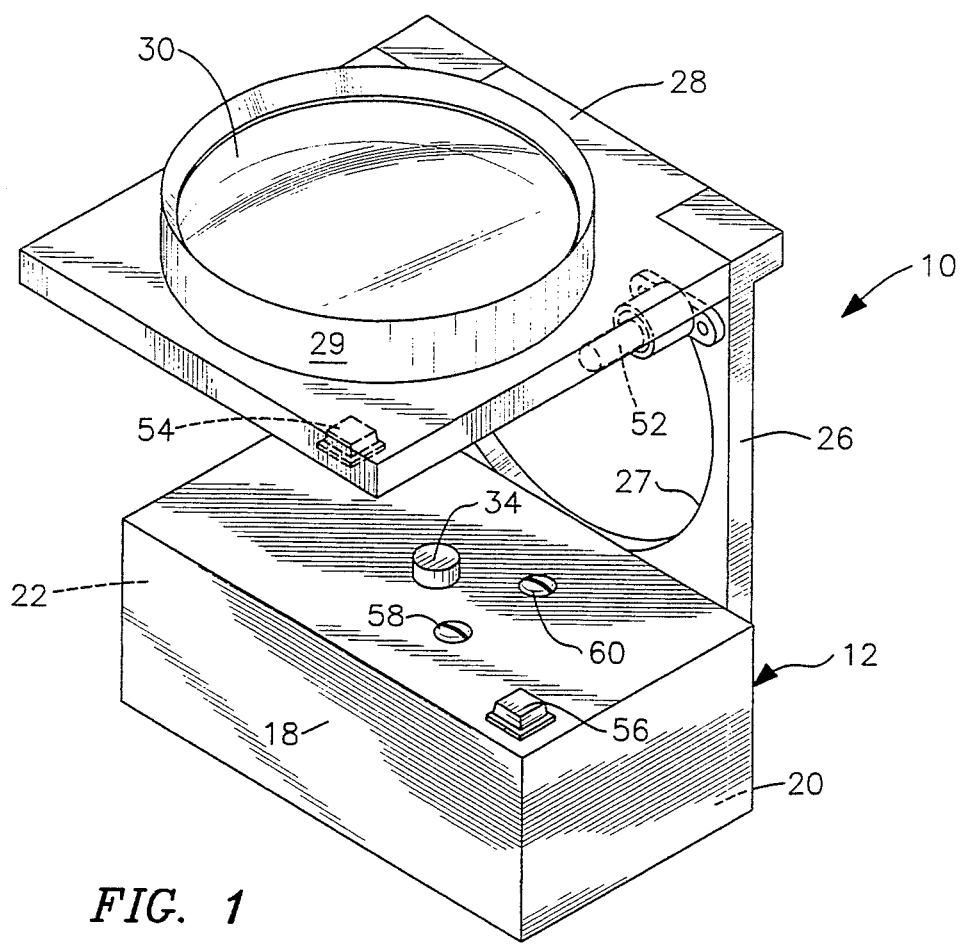
FIG. 1 is a perspective view of an exemplary embodiment of the invention.
Figure 2:
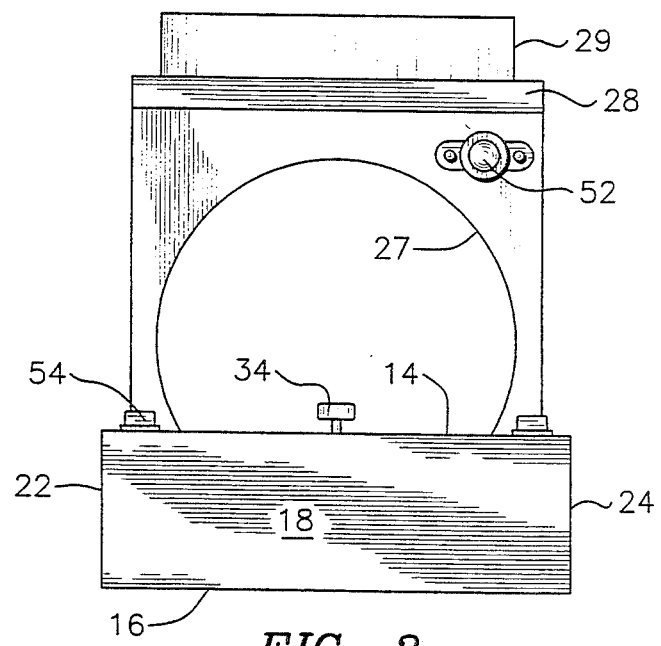
FIG. 2 is a front elevational view thereof.

Referring now to FIGS. 1 and 2, it will there be seen that an exemplary embodiment of the invention is denoted by the reference numeral 10 as a whole.

Loose stone detector 10 includes a hollow housing 12 of parallelpiped construction. Housing 12 includes a top wall 14, a bottom wall 16, a front wall 18, a rear wall 20, and side walls 22, 24. An upstanding spacer wall 26 is secured to and overlies rear wall 20; it supports cantilevered support wall 28 which carries annular magnifying lens frame 29 which in turn holds magnifying lens 30. The length of support wall 28 is substantially equal to the focal length of magnifying lens 30 so that items in the proximity of housing top wall 14 are clearly magnified by said lens.

Figure 3:
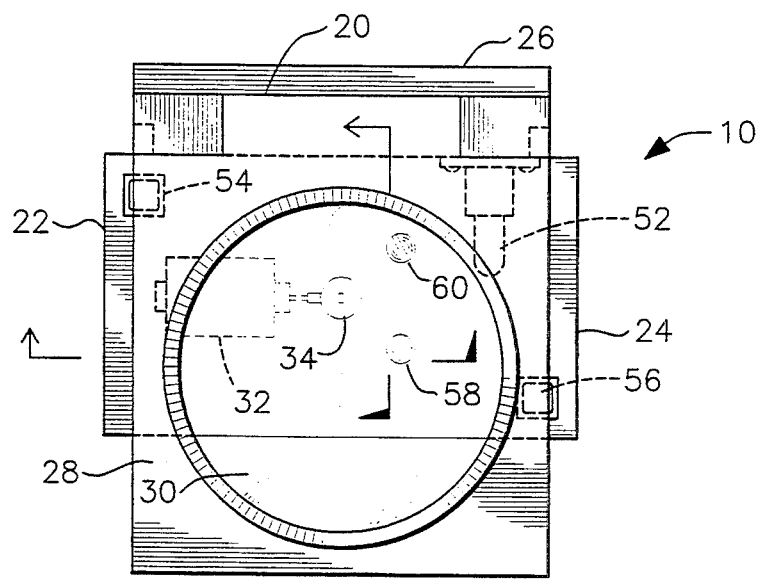
FIG. 3 is a top plan view thereof.
Figure 4:
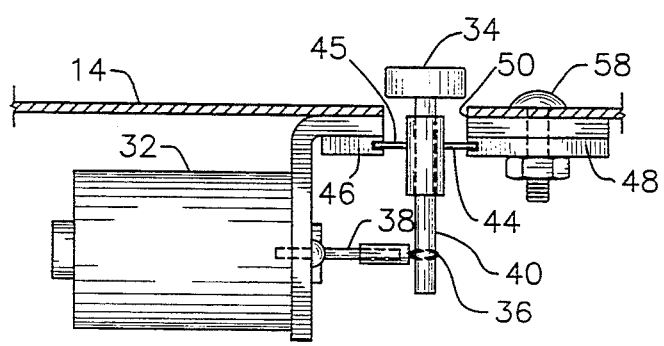
FIG. 4 is a sectional view taken along line 4—4 in FIG. 3.

Vibrating means 32 (FIGS. 3 and 4) is housed within housing 12 and is connected to pedestal 34 through an assembly of parts including offset crankshaft 36 which is connected to output shaft 38, vertical shaft 40, and tubing 42 that loosely ensleeves said vertical shaft 40. Pins 44 and 45 engages tubing 42 on diametrically opposite sides thereof; said pins do not extend through shaft 40. The respective free ends of pins 44 and 45 are received within plates 46 and 48, respectively, and are secured against movement thereby because said plates are fixedly secured to the underside of housing top wall 14 by screw members 58, 60, or other suitable fastening means. Thus, activation of vibrating means 32, which may be provided in the form of a 24,000 rpm twelve volt direct current motor, effects vibration of pedestal 34. More particularly, shaft 40 and pedestal 34 move because of the connection of shaft 40 to offset crankshaft 38, and tubing guide 42 constrains the movement of shaft 40, thereby creating a vibration as said shaft 40 beats against the inner cylindrical sidewalls of said tubing guide 42. The tubing guide does not vibrate because of its mounting to housing 12 through pins 44 and 45.

Figure 5:
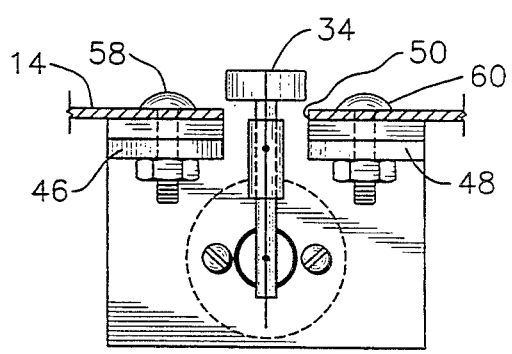
FIG. 5 is a sectional view taken along line 5—5 in FIG. 3.

Pedestal 34 extends a short distance through an aperture 50 (FIGS. 4 and 5) formed in top wall 14 so that an item of jewelry may be placed in abutting relation to said pedestal. An illumination means 52 is mounted to the underside of magnifying lens frame 28 and is activated upon actuation of a first switch actuator 54. A second switch actuator 56 actuates vibrating means 32.

A large aperture 27 formed in upstanding support wall 26 admits ambient light therethrough to further enhance the viewing of the item of jewelry. Moreover, cantilevered support wall 28 may be hingedly secured to spacer wall 26 to facilitate storage of device 10 when it is not in use.

Numerous vibrating means are also within the scope of this invention. For example, a harmonic vibrator that changes up and down motion into circular motion may be used. Moreover, numerous mechanical linkages may be employed to interconnect motor 32 and pedestal 34; this invention is not limited to the specific linkage disclosed herein.

To use the novel device, light 52 is first activated by pressing switch actuator 54. A ring or other jewelry item having one or more stones in a setting is then held with a thumb and index finger lightly against pedestal 34, and vibrating means 32 is activated by pressing switch actuator 56. Alternatively, if a customer is unable or unwilling to remove a ring, the ring may still be placed lightly against said pedestal while still on the customer's finger. Even before the vibrating means is activated, both the customer and the jeweler may inspect the illuminated jewelry item under the magnifying lens for signs of wear. Upon activation of the vibrating means, any stones that are loose will jiggle, rotate, or otherwise vibrate, and both the customer and the jeweler will be able to see such movement. Very short bursts of activation of switch actuator 56 provide the best results. Upon seeing the jiggling or rotation of the stone or stones, the customer does not argue with the jeweler as to whether or not a repair is needed. Thus, little or no training is required before novice jewelers can use novel device 10; even part-time employees of a retail establishment who are not jewelers can use the device. The customers get to see for themselves whether or not their stones are loose, and this eliminates a major point of contention between jewelry repair service personnel and their customers. Significantly, a ring or other jewelry item can be checked at a counter within seconds. This facilitates the screening of a much higher volume of rings because customers who would not normally ask a jeweler to inspect their rings will voluntarily submit their rings to testing by the novel device just because they see other people using it. Even if the stones are found to be securely set, the magnifying lens enables the customer and the service representative to see other problems of the type caused by wear, as mentioned earlier. Thus, there are a number of advantages associated with the novel device.

It will thus be seen that the objects set forth above, and those made apparent by the foregoing description, are efficiently obtained and since certain changes may be made in the above construction without departing from the teachings and suggestions of the invention, it is understood that all such changes or modifications are within the scope of this invention.

What is claimed is:

1. A device for detecting loose stones in a jewelry setting, comprising:
   a magnifying lens having a predetermined focal length;
   a pedestal disposed a predetermined distance away from said magnifying lens, said predetermined distance being substantially equal to the predetermined focal length of said magnifying lens;
   vibrating means attached to said pedestal for causing said pedestal to vibrate; and
   a switch actuator for activating said vibrating means;
   whereby an item of jewelry having at least one stone in a setting is positioned lightly against said pedestal and said vibrating means is activated so that the response of the stone to vibration of the pedestal may be observed through said magnifying lens.

2. The device of claim 1, further comprising:
   a base member for housing said vibrating means;
   a support wall for holding said magnifying lens; and
   a spacer wall for interconnecting said base member and said support wall, said spacer wall having a length substantially equal to the predetermined focal length of said magnifying lens.

3. The device of claim 2, further comprising:
   a light means for illuminating said pedestal and a jewelry item positioned thereagainst; and
   a switch actuator for activating said light means.

4. The device of claim 3, wherein said light means is mounted to an underside of said support wall.

5. The device of claim 4, wherein said vibrating means includes a motor having an output shaft and a linkage means for interconnecting said output shaft to said pedestal, said linkage means having a structure that imparts vibration to said pedestal.

6. The device of claim 5, wherein said linkage means comprises:
   a pedestal-supporting shaft having a first end to which said pedestal is attached;
   an offset crankshaft secured to said output shaft of said motor and to a second end of said pedestal-supporting shaft;
   a tubing guide that loosely slideably receives said pedestal-supporting shaft; and
   mounting means for securely mounting said tubing guide to said housing so that activation of said motor effects vibration of said pedestal.

7. The device of claim 6, wherein said mounting means includes a pair of pins having their innermost ends secured to said tubing guide and having their outermost ends secured to said housing, said pair of pins holding said tubing guide against movement.

* * * * *